United States Patent [19]

Miller

[11] Patent Number: 5,997,560
[45] Date of Patent: *Dec. 7, 1999

[54] SURGICAL CUTTING INSTRUMENT

[75] Inventor: Michael E. Miller, Indianapolis, Ind.

[73] Assignee: SDGI Holdings, Inc., Wilmington, Del.

[ * ] Notice: This patent is subject to a terminal disclaimer.

[21] Appl. No.: 09/118,045

[22] Filed: Jul. 17, 1998

Related U.S. Application Data

[63] Continuation of application No. 08/278,558, Jul. 21, 1994, Pat. No. 5,782,849.

[51] Int. Cl.$^6$ .................................................. A61B 17/00
[52] U.S. Cl. ............................................ 606/170; 604/22
[58] Field of Search ............................. 604/22; 606/159, 606/170, 171, 180

[56] References Cited

U.S. PATENT DOCUMENTS 5,782,849 7/1998 Miller ....................................... 606/170

*Primary Examiner*—Michael Buiz
*Assistant Examiner*—William W. Lewis
*Attorney, Agent, or Firm*—Baker & Daniels

[57] ABSTRACT

A surgical cutting instrument for cutting joint tissue includes an outer tubular member, or cannula, sized for percutaneous insertion into an anatomical space, such as s joint space in the spine. The outer tubular member has a cutting opening at its blunt-tipped distal end. The proximal end is supported by a handpiece. A cutting member is slidably disposed within the outer tubular member and includes a tubular cutting head portion defining an end opening and a cutting edge at the end opening. In the specific embodiment, the cutting member is a tubular tubular member having a cutting head portion at its distal end and a body portion extending therefrom to the handpiece. A hinge is integrally formed in the tubular cannula to connect the cutting head portion with said body portion, to permit pivoting of the cutting head portion relative to the body portion. As the cutting member is reciprocated within the outer cannula, the cutting edge contacts tissue drawn into the cutting opening. Resistance from the tissue causes the cutting head to pivot about the hinge to form an essentially zero clearance between the cutting head and the cutting opening in the outer cannula.

29 Claims, 3 Drawing Sheets

SURGICAL CUTTING INSTRUMENT

This application is a continuation of application Ser. No. 08/278,558 filed Jul. 21, 1994, now U.S. Pat. No. 5,782,845.

BACKGROUND OF THE INVENTION

The present invention relates to a percutaneous or intratrocar surgical instrument for the excision and removal of a wide range of tissues. More particularly, a surgical cutting instrument is disclosed which is particularly adapted for a wide range of operating speeds and which is capable of cutting tough tissue, such as may be found during orthopaedic or spinal surgery. The present invention has application in a wide range of procedures, although the following disclosure will pertain principally to minimally invasive cutting instruments used in the orthopaedic or spinal surgical fields.

In the field of spinal surgery, one problem that is frequently diagnosed and treated concerns degeneration or herniation of the intervertebral disk. In the past, treatment of these diagnosed conditions has required complicated and highly invasive surgical procedures, often involving some degree of fusion between adjacent vertebrae serviced by the affected intervertebral disk. In these procedures it is important that the affected disk be entirely removed for replacement by bone graft material. In some cases, a prosthetic disk may be implanted.

Within the last decade, techniques for percutaneous diskectomies have been developed. One such system is described in the patent to Onik, U.S. Reissue Pat. No. 33,258. The Onik device, like other known devices, is a "tube within a tube" cutting instrument which incorporates a reciprocating inner cutting sleeve operating within the central bore of an outer cutting sleeve. Typically, the excised disk material is suspended in a saline irrigation fluid which is aspirated through the central passageway of the inner cutting sleeve.

Similar cutting devices are represented in U.S. Pat. No. 4,246,902 to Martinez, and U.S. Pat. No. 5,106,364 to Hayafuji. While these aforementioned devices utilize linearly reciprocating cutters, another genre of surgical instruments implement a rotary cutting action. Such a device is represented by the patent to Bonnell et al., U.S. Pat. No. 4,203,444.

The tissue cutting instruments presently available in the art suffer from a variety of problems. For example, rotary cutters have a tendency to become clogged as the excised tissue "spools" or winds around the shaft driving the rotating cutter blade. This spooling can clog the aspiration channel of the cutter and even stall the blade or motor.

Another problem common between rotary and linearly reciprocating devices is their general inability to cut very tough tissue, at least using an instrument that is adapted for percutaneous insertion. Certainly larger cutting instruments driven by larger motors are capable of cutting very tough or hard tissue. However, no prior device has been able to avoid the trade-off between a minimally invasive cutting instrument and the ability to cut these types of tough tissue.

There is a need in the field of tissue excision and removal for a surgical cutter that is adapted for minimally invasive uses, but that is still capable of cutting hard or tough tissue encountered in spinal and orthopaedic procedures, for example. The cutting instrument must be capable of excising the tissue cleanly, without tearing, and of aspirating the tissue pieces efficiently and without clogging. These and other needs in the industry are addressed by the present invention.

SUMMARY OF THE INVENTION

A surgical cutting instrument is provided for cutting tissue inside a joint space, such as disk material between two vertebrae. The instrument has further application for cutting tissue in other anatomical spaces, for instance the gall bladder or prostate. The instrument includes an outer cannula sized for percutaneous insertion into the joint space. The outer cannula has a cutting opening at its blunt-tipped distal end and is supported at its proximal end by a handpiece. A cutting member is slidably disposed within the outer cannula which includes a tubular cutting head portion defining an end opening and a cutting edge at the end opening.

In one specific embodiment, the cutting member is a tubular cannula having a cutting head portion at its distal end and a body portion extending therefrom to the handpiece. A hinge is integrally formed in the tubular cannula to connect the cutting head portion with said body portion, to permit pivoting of the cutting head portion relative to the body portion. As the cutting member is reciprocated within the outer cannula, the cutting edge contacts tissue drawn into the cutting opening. Resistance from the tissue causes the cutting head to pivot about the hinge to form an essentially zero clearance between the cutting head and the cutting opening in the outer cannula.

Preferably, the cutting member is a single tubular cannula. A diametrical slot is defined in the cannula to form a hinge segment separating the cutting head and body portions of the cutting member. In the preferred embodiment, the slot extends through about 90% (ninety percent) of the inner cannula diameter. It has been found that this slot configuration yields a hinge segment that is strong enough to withstand cyclic loading yet flexible enough to allow the cutting head portion to pivot when resisted by tissue in the cutting opening.

The tubular cutting member defines an aspiration passageway and is connected at its proximal end to a vacuum source. The vacuum draws tissue through the cutting opening in the outer cannula. As the inner cutting member is stroked toward the distal end of the cannula, its cutting edge contacts the tissue projecting into the outer cannula. The tissue inherently resists the cutting motion of the member, so that as the cutting member continues in its stroke the cutting head portion is pushed or pivoted toward the cutting opening of the outer cannula. The greater the force applied to the tissue, the greater the pivoting of the cutting head portion, until a zero clearance condition is established between the inner and outer cutting edges. The tissue is then effectively and completely sheared and aspirated back through the instrument.

In another embodiment, the inner cutting member or cannula includes a support segment extending from the hinge segment. This support segment is essentially an extension of the hinge segment along the remaining length of the inner cutting member. Only the cutting head in this embodiment constitutes a full cylindrical segment. One advantage realized by this embodiment, in addition to the hinge effect previously described, is a reduction in the sliding friction between the reciprocating inner cutting member and the outer cannula.

A further embodiment contemplates a longitudinal slot in the cutting head, in combination with the circumferential slot forming the hinge segment. This longitudinal slot extends from the cutting edge of the inner cutting member to the circumferential hinge slot to permit circumferential expansion or contraction of the cutting head. Circumferential expansion of the cutting head (that is by widening the longitudinal slot) further ensures a zero clearance between the cutting edge of the inner member and the cutting opening of the outer cannula. Circumferential contraction of the cutting head on the return stroke can reduce sliding friction between the reciprocating inner member and the outer cannula.

One object of the present invention is to provide a surgical cutting instrument that is adapted for percutaneous insertion into an anatomical space, such as a joint space in the spine. A further object resides in providing such an instrument that can cleanly and efficiently excise unwanted tissue without clogging and without tearing the subject tissue.

Yet another object is achieved by one feature of the invention providing for a single piece tubular cutting member with a hinge formed in the member. Other objects, benefits and advantages of the invention will become apparent from the following written description and accompanying figures.

DESCRIPTION OF THE PREFERRED EMBODIMENTS

Figure 1:
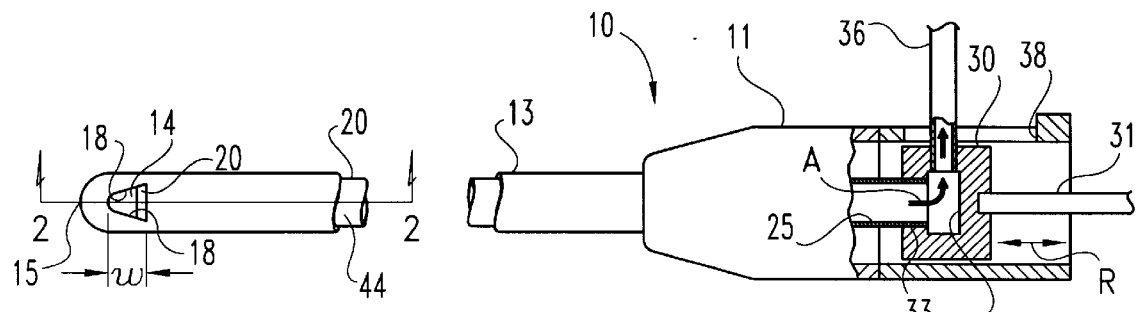
FIG. 1 is a partial cutaway view of a surgical cutting instrument in accordance with a preferred embodiment or the present invention.

For the purposes of promoting an understanding of the principles of the invention, reference will flow be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

A surgical cutting instrument 10 is shown in FIG. 1 which is adapted for percutaneous insertion at the surgical site, and is specifically adapted to cut tissue in the spinal region. However, the same instrument could be used in other orthopaedic, such as an arthroscopic surgery of the knee, or similar surgical procedures, such as removal of the gall bladder or prostate. The instrument 10 includes a hand piece 11 which supports an outer cannula 13. The outer cannula has a blunt distal tip 15 to minimize trauma to tissue as the cutting instrument is manipulated in the surgical site. The outer cannula 13 includes a cutting opening 14 formed therethrough which opens to a central bore 16 extending through the length of the cannula 13. The cutting opening 14 defines a cutting edge 18, which in the preferred embodiment is defined by a beveled cut in the wall of the outer cannula. In the preferred embodiment, the cutting opening 14 is in the shape of an isosceles triangle. The cutting edge 18 in the specific embodiment is defined at the side of the triangle, but excludes the base of the triangular shape as shown in FIG. 1.

The cutting instrument 10 further includes an inner cannula 20 which is slidably and concentrically disposed within the outer cannula 13. The inner cannula 20 terminates in a cutting edge 22 at the end opening 23 of the cannula. The end opening 23 opens into an aspiration passageway 25 extending through the entire length of the inner cannula 20.

Figure 2:
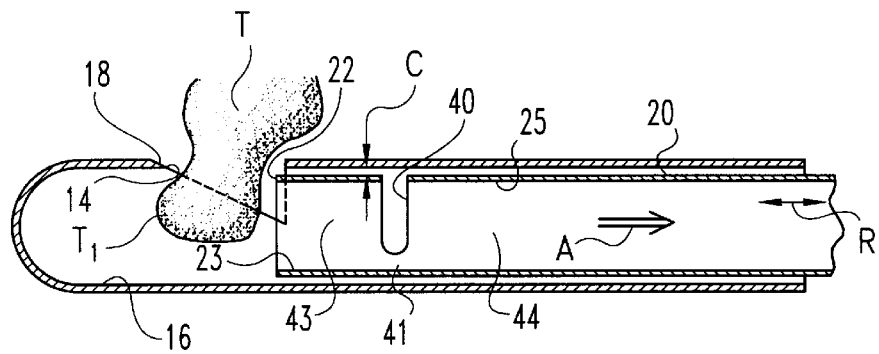
FIG. 2 is a side cross-sectional view of the cutting instrument in FIG. 1, taken along line 2—2 as viewed in the direction of the arrows.

The outer cannula 13 is supported by the hand piece 11, while the inner cannula 20 also extends into the hand piece 11 to engage a drive mount 30 at a cannula support portion 33. The drive mount is engaged to a drive rod 31 that is connected to a motor or suitable mechanism for providing reciprocating motion. Specifically, the drive rod 31 and mount 30 reciprocate axially in the direction of the arrows R shown in FIGS. 1 and 2. Since the inner cannula 20 is fixed to the drive mount 30 it too reciprocates within the outer cannula 13. As the inner cannula 20 reciprocates, the inner surface of the outer cannula and the outer surface of the inner cannula operate as a bearing surface for the smooth movement of the inner cannula.

The drive mount 30 includes an aspiration chamber 34 which is connected through an aspiration tube 36 to a suitable vacuum source and tissue collection chamber in a manner well known in the art. In this particular embodiment, the aspiration tube 36 is engaged to the reciprocating drive mount 30. This aspect requires the definition of a slot 38 in the hand piece 11 to allow the tube 36 room to move as it reciprocates with the drive mount.

As thus far described, the instrument 10 incorporates many features of known reciprocating cutters, particularly those implementing the "tube within a tube" approach. However, it has been found that these types of cutters are inherently limited in the type of tissues that can be cut and in the cutting speeds at which they are capable of operating. The present invention provides a means to allow the cutting instrument 10 to cut much tougher tissue than prior art devices, while still maintaining the minimally invasive dimensions of the instrument for percutaneous or intratrocar insertion. More specifically, the inner cannula 20 includes a hinge slot 40 cut circumferentially around the cannula. The hinge slot 40 defines a hinge segment 41 at the uncut portion of the cannula. This hinge segment 41 is, in essence, a narrow arc segment of a tubular formed inner cannula. The slot 40 further defines a cutting head 43 connected by the hinge segment 41 to the remaining body portion 44 of the cannula 20.

Figure 3:
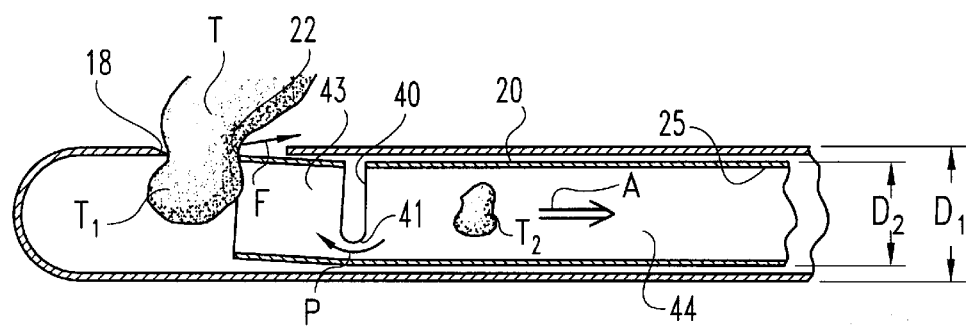
FIG. 3 is a side cross-sectional view similar to the view in FIG. 2 depicting the instrument with the blade positioned to cut a segment of tissue.

The particular benefit of this configuration for the inner cannula 20 is depicted more clearly in FIG. 3. (It is understood that the relative dimensions of the cutter components have been exaggerated for clarity.) It is known that as a reciprocating cutter engages and attempts to severe tissue T drawn into the cutting opening the tissue inherently resists the cutting action. As a portion of tissue $T_1$ is being severed, it exerts a reactive force F against the cutting edge 22 of the inner cannula 20. In a typical tube within a tube reciprocating cutter, this reactive or resistive force F is withstood by the cannula without any significant bending or movement of the solid inner cannula. Thus, with prior devices the clearance between the cutting edge remains constant, which permits a strand of tissue to remain in the gap between the inner and outer tubes. Frequently, the tissue is not excised on the first stroke of the cutting blade.

In accordance with the present invention, with the introduction of the hinge slot 40 and hinge segment 41 the cutting head 43 is permitted to pivot in the direction of the arrow P in FIG. 3. As the inner cannula 20 advances toward the cutting opening 14 of the outer cannula, it maintains a clearance C between the two tubes. Once the cutting head 43 contacts the tissue it pivots so that the cutting edge 22 forms a zero clearance interface with the cutting edge 18 of the outer cannula cutting opening 14. This zero clearance facilitates cutting the tissue segment $T_1$, completely severing a strand of tissue between the inner and outer cannulae. This feature eliminates the gap, typically exists between the cutting edges of the prior art devices. With the hinge segment 41 and pivot capability for the cutting head 43 of the present invention, a fully efficient cut is made and the subject tissue $T_1$ is completely and cleanly cut from the main body of tissue T. The excised tissue $T_2$ is then drawn in the direction of the arrow A through the end opening 23 and the aspiration passageway 25 defined through the body portion 44 of the inner cannula.

In the preferred embodiment, each of the cutting components, specifically the outer cannula 13 and the inner cannula 20, are formed of stainless steel, preferably 304SS typically used in medical grade components. In prior art devices, it is generally critical to maintain exact dimensions of the outer and inner cannula. Ideally, a zero clearance between the two components is desired to permit a more efficient cutter. However, the zero clearance also results in high friction which reduces the speed capability of the instrument or requires a higher power motor to reciprocate the inner cannula within the outer cannula. On the other hand, larger tolerances make the problem of tissue strands even greater as the tissue has more room to "hide" from the cutting edges. Prior art devices must wrestle with these clearance issues. With the present invention, the requirements for high a tolerance close fit between the inner and outer cannula components is eliminated. It has been found that the hinge slot 40 and hinge segment 41 readily accommodate cutting instruments which are toleranced to +0.025 mm on both the inner diameter of the outer cannula and the outer diameter of the inner cannula.

In one specific embodiment, the cutting opening 14 has a width W, as shown in FIG. 1, that is equal to approximately one half the inner diameter $D_1$ (see FIG. 3) of the outer cannula 13. The cutting opening 14 is placed as close to the rounded distal tip 15 as possible. To readily permit percutaneous insertion of the instrument, the outer diameter of the outer cannula 13 is preferably less than about 5 mm. Thus, this dimension would dictate a cutting opening width W of about 2½ mm.

Figure 4:
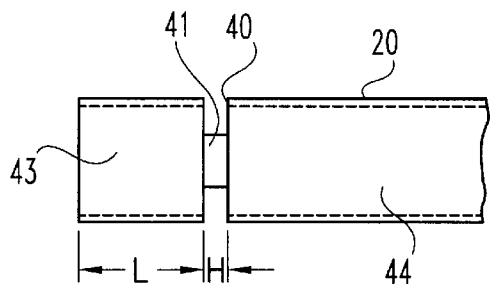
FIG. 4 is a top elevational view of the inner cutting member or cannula showing the cutting head and hinge segment.

The cutting head 43 of the inner cannula 20 has a length L (FIG. 4) which is long enough to allow the entire width of the cutting opening 14 to be occluded at the end of the stroke of the inner cannula 20. Thus, the length L of the cutting head 43 is at least equal to the cutting opening width W in the outer cannula 13. The slot 40 that defines the hinge segment 41 extends through about 90% of the inner cannula diameter. Thus, the arc hinge segment 41 subtends an angle of about 70–80° with a chord length of about ½ the diameter $D_2$. The hinge segment 41 has a length H which is preferably about one fourth the diameter $D_2$ of the inner cannula 20. The length H of the hinge segment 41 must be long enough to permit pivoting of the cutting head 43 in the direction P as the tissue is cut, yet strong enough to withstand cyclic bending as the cutter is used. In one specific embodiment, the length H of the hinge segment 41 is about 0.75 mm for a cutter driven by a motor capable of operation at speeds ranging between 15 to 250 strokes per second. The hinge will flex twice for each cycle as the cutting head pivots up to cut and back down on the return stroke. The arc configuration of the hinge segment 41 increases its stiffness fatigue capability.

Figure 5:
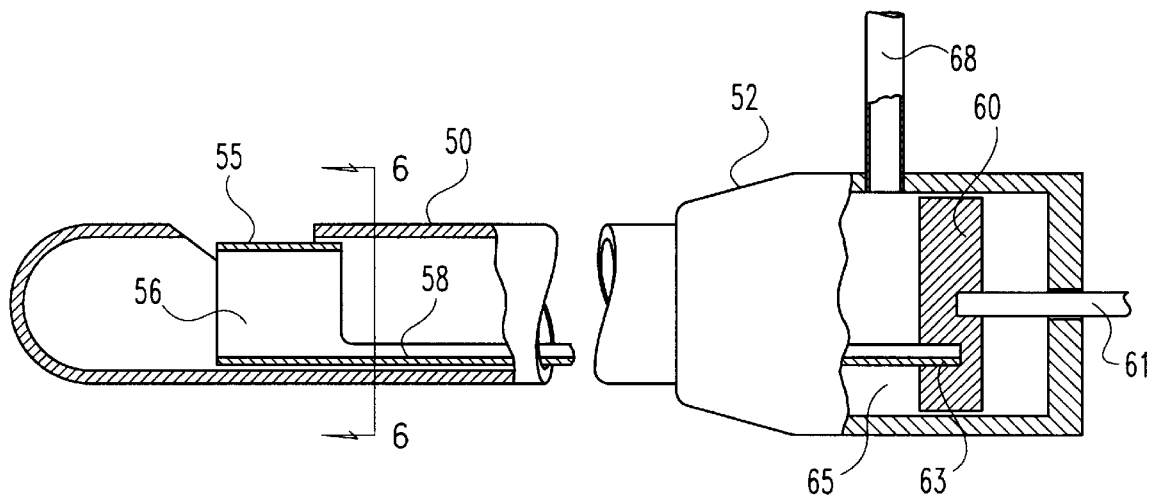
FIG. 5 is a side partial cutaway view of an alternative embodiment to the surgical cutting instrument of the present invention.
Figure 6:
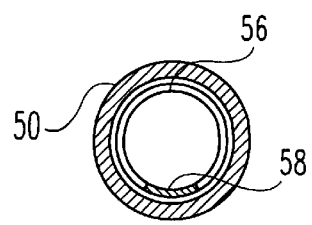
FIG. 6 is a cross sectional view of the cutting head of the alternative embodiment, taken along line 6—6 as shown in the direction of the arrows in FIG. 5.

An alternative embodiment of the surgical cutting instrument of the present invention is shown in FIGS. 5 and 6. In this embodiment, an outer cannula 50 is provided which is substantially similar in construction to the outer cannula 13 previously described. Likewise, a hand piece 52 is provided for supporting the outer cannula. The inner cannula 55 of this embodiment is modified somewhat from the previous embodiment. This configuration includes a cutting head 56 which is sized and shaped similar to the cutting head 43 of the embodiment in FIGS. 2 and 3. With this inner cannula 55, however, the hinge segment is extended through most of the length of the inner cannula to define a body portion 58. Specifically, the body portion is defined by an arc segment from a tubular form, preferably subtending an angle of about 70–80°. This body portion 58 is engaged to a drive mount 60 which is itself engaged to a drive rod 61 to provide an axial reciprocating movement to the cutting head 56. The hand piece 52 defines an aspiration chamber 65 which is connected by an aspiration tube 68 to a vacuum source. The aspiration chamber 65 open directly to the interior of the outer cannula, thereby providing a greater aspiration flow path.

In this embodiment, it can be seen that the inner cannula 55 includes a full cylindrical segment only at the cutting head 56. Thus, the cutting head 56 will exhibit the same pivoting aspect about the body portion 58 as with the previous embodiment. However, the reduced profile of the inner cannula throughout most of its length, achieved by the arc form of the body portion 58, reduces the sliding friction between the inner cannula 55 and the outer cannula 50. This embodiment retains the benefit of pivoting the cutting edge of the cutting head into a zero clearance with the cutting opening of the outer cannula 50 as the tissue is being excised. One further advantage is that a smaller motor can be used to drive the entire cutting assembly. This specific embodiment is preferably reserved for less rigorous tissue.

Figure 7:
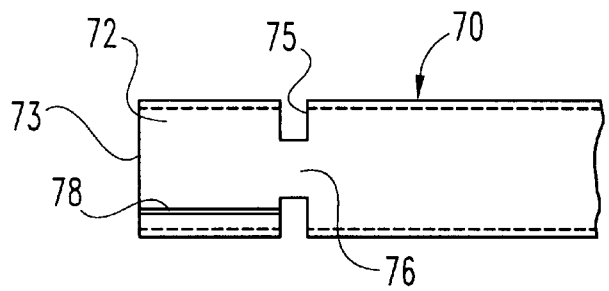
FIG. 7 is a bottom elevational view of another embodiment of the inner cutting member showing a cutting head similar to that depicted in FIG. 4 with the provision of a longitudinal slot.
Figure 8:
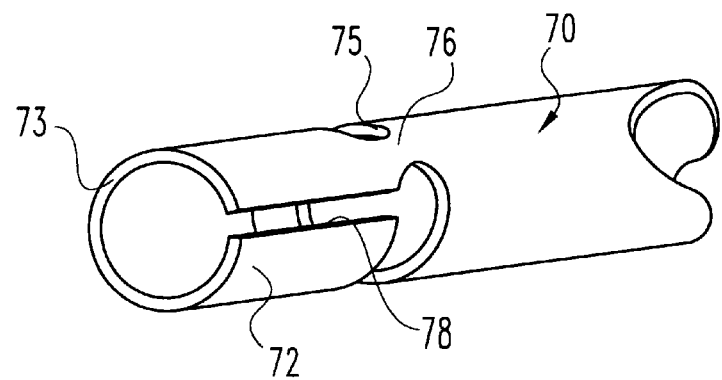
FIG. 8 is a pictorial representation of the inner cutting member of FIG. 7.

An inner cutting member 70 of an alternative embodiment of the invention is shown in FIGS. 7 and 8. It is understood that this cutting member 70 is reciprocatingly disposed within an outer cannula, such as cannula 13, in a manner similar to the previous embodiments. The cutting member 70 is similar to the member 20 shown in FIG. 4. For example, the inner cutting member 70, or inner cannula, includes a cutting head 72 with a cutting edge 73. The cutting head 72 is formed by the provision of a circumferential slot 75 defined in the cutting member 70. The slot further forms a hinge segment 76 so that the cutting head 72 is capable of the same hinged cutting performance as the previous embodiments.

The present embodiment, however, contemplates the addition of a longitudinal slot 78 in the cutting head 72. Specifically, the longitudinal slot 78 extends from the cutting edge 73 to the circumferential hinge slot 75. The slot 78 is preferably, but not necessarily, defined parallel to the longitudinal axis of the inner cutting cannula 70. The longitudinal slot 78 permits circumferential expansion or contraction of the cutting head 72. Circumferential expansion further ensures a zero clearance between the cutting edge 73 and the cutting opening of the outer cannula. Circumferential contraction on the return stroke of the inner cannula 70 reduces the sliding friction between the inner and outer members.

In one aspect, the circumferential expansion of the cutting head 72 occurs during the cutting stroke. As the cutting head encounters resistance from the tissue extending through the outer cannula cutting opening, the head pivots upward about the hinge segment 76. It is further contemplated that the longitudinal slot 78 can widen against the resistance of the tissue, thereby allowing the cutting head to circumferentially expand against the outer cannula. Alternatively, the cutting head 72 can be preformed so that the cutting head is expanded into contact with the outer cannula when the cutting instrument is assembled. For a variety of reasons, it is either difficult or undesirable to use an inner cannula having an outer diameter that is exactly equal to the inner diameter of the outer cannula. Manufacturing tolerances dictate that the nominal diameter of the inner cannula be less than the inner diameter of the outer cannula. Moreover, a smooth sliding fit between the two cannula further requires some clearance between the two components. These same considerations, however, decrease the cutting efficiency of the cutting edge of the inner cannula against the cutting opening of the outer cannula. The longitudinal slot 78 can be preformed with the slot expanded so that the cutting head has a diameter greater than the rest of the inner cutting cannula. This further ensures a zero clearance at the cutting interface between inner and outer cutting edges.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. This invention contemplates a reciprocating cutter having a hinged cutting head portion. While the preferred embodiments encompass an inner cannula constructed with the hinge integrally formed between the cutting head and the body of the cannula, alternative hinge constructions are contemplated. For example, the cutting head portion may be separate from the body of the inner cannula with a hinge connecting the two parts.

What is claimed is:

1. A surgical cutting instrument for use in cutting tissue within an anatomical space comprising:

an outer tubular member sized for percutaneous insertion into the anatomical space, said outer tubular member defining a central bore along the length thereof and having a proximal end and a distal end, said outer tubular member further defining a cutting opening sized to receive tissue therethrough and having a first a cutting opening sized to receive tissue therethrough and having a first cutting edge adjacent said distal end;

a cutting member slidably disposed within said central bore of said outer tubular member, said cutting member including;

a tubular cutting head portion defining an end opening and a second cutting edge at said end opening;

a body portion extending through said central bore, said body portion having a distal end adjacent said cutting head portion and an opposite proximal end;

a drive mount connected to said proximal end and engageable to a drive source to reciprocate said second cutting edge relative to said first cutting edge; and a hinge portion connecting said cutting head portion with said body portion to permit pivoting of said cutting head portion relative to said body portion, whereby said cutting head portion pivots about said hinge portion toward said cutting opening when said cutting head contacts tissue extending through said cutting opening to form an essentially zero clearance between said second cutting edge and said first cutting edge as said cutting member is advanced toward said distal end of said outer tubular member.

2. The surgical cutting instrument according to claim 1, wherein:

said cutting member is tubular;

said body portion and said cutting head portion are integral; and said hinge portion includes a diametrical slot defined in said tubular cutting member to form a hinge segment connecting said body portion and said cutting head portion, said hinge segment defining an arc segment from a tubular form.

3. The surgical cutting instrument according to claim 2, wherein said diametical slot extends through about 90% (ninety percent) of the diameter of said tubular cutting member.

4. The surgical cutting instrument according to claim 2, wherein said hinge segment subtends an arc angle of between about 70 degrees and about 80 degrees (70–80°).

5. The surgical cutting instrument according to claim 2, wherein said hinge segment has a length dimension about one-fourth (¼) the diameter of said tubular cutting head.

6. The surgical cutting instrument according to claim 2, wherein said cutting head defines a slot extending across said cutting head from said second cutting edge to said diametrical slot.

7. The surgical cutting instrument according to claim 1, wherein:

said body portion of said cutting member is tubular and defines an aspiration passageway therethrough.

8. The surgical cutting instrument according to claim 7, wherein:

said cutting head portion, said body portion and said hinge portion are integral; and said cutting head defines a slot extending across said cutting head from said second cutting edge to said hinge portion.

9. The surgical cutting instrument according to claim 1, wherein:

said cutting opening has a width dimension along the length of said outer tubular member; and said cutting head portion has a length dimension along the length of said cutting member, wherein said length dimension is at least equal to said width dimension.

10. The surgical cutting instrument according to claim 1, wherein:

said cutting head portion, said body portion and said hinge portion are integrally formed;

said cutting head portion is tubular; and said hinge portion and said body portion are defined by an arc segment from a tubular form extending from said cutting head portion to said connecting means.

11. The surgical cutting instrument according to claim 10, wherein said arc segment defining said hinge portion and said body portion subtends an arc angle of between 70 degrees and 80 degrees (70–80°).

12. Tie surgical cutting instrument according to claim 10, wherein said cutting head defines a slot extending across said cutting head from said second cutting edge to said hinge portion.

13. A surgical cutting instrument for use in cutting tissue, comprising:
- an outer tubular member defining a central bore therethrough and a cutting opening at one end thereof in communication with said central bore, said cutting opening having a first cutting edge; and
- a cutting member slidably disposed within said central bore of said outer tubular member and including;
  - a cutting head portion having a second cutting edge configured to cooperate with said first cutting edge to excise tissue therebetween;
  - a body portion extending through at least a portion of said central bore and having a distal end adjacent said cutting head portion and an opposite proximal end;
  - means for connecting said proximal end to a drive source to reciprocate said cutting member relative to said first cutting edge; and
  - a hinge portion connecting said cutting head portion to said body portion to permit pivoting of said cuffing head portion relative to said body portion when said cutting head portion contacts tissue extending through said cutting opening as said cutting member is advanced toward said first cutting edge.

14. The surgical cutting instrument according to claim 13, wherein said cutting head portion is tubular and defines an end opening, said second cutting edge being defined at said end opening.

15. The surgical instrument according to claim 14, wherein said hinge portion defines an arc segment from a tubular form.

16. The surgical instrument according to claim 15, wherein said arc segment subtends an angle of between about 70 degrees and about 80 degrees (70–80°).

17. The surgical instrument according to claim 15, wherein said arc segment has a length dimension about one-fourth (¼) the diameter of said tubular cutting head portion.

18. The surgical cutting instrument according to claim 13, wherein:
- said cutting opening of said outer tubular member has a width dimension along the length of said tubular member; and
- said cutting head portion has a length dimension along a length of said cutting member that is at least equal to said width dimension of said cutting opening.

19. The surgical cutting instrument according to claim 13, wherein:
- said cutting member is tubular;
- said body portion and said cutting head portion are integral; and
- said hinge portion includes a diametrical slot defined in said tubular cutting head portion, said hinge segment defining an arc segment from a tubular form.

20. The surgical cutting instrument according to claim 19, wherein said diametrical slot extends through about 90% (ninety percent) of the diameter of said tubular cutting member.

21. The surgical cutting instrument according to claim 13, wherein said body portion is tubular and defines an aspiration channel therethrough.

22. The surgical cutting instrument according to claim 13, wherein said cutting opening has a transverse dimension along the circumference of said outer tubular member sized to permit said cutting head portion pivoting about said hinge portion at least partially into said cutting opening.

23. A surgical cutting instrument for use in cutting tissue, comprising:
- an outer tubular member defining a central bore therethrough and a cutting opening at one end thereof in communication with said central bore, said cutting opening having a first cutting edge; and
- a cutting member slidably disposed for reciprocation within said central bore and including;
  - a cutting head portion having a second cutting edge configured to cooperate with said first cutting edge to excise tissue therebetween; and
  - means connected to said cutting head portion for pivoting said cutting head portion within said central bore as said cutting head portion contacts tissue extending through said cutting opening when said second cutting edge is advanced toward said first cutting edge.

24. A cutting element for use in a surgical cutting instrument having an outer tubular member defining a central bore and a cutting opening in communication with the central bore, said cutting element comprising:
- a cutting member slidably disposable within the central bore of the outer tubular member, said cutting member including;
  - a cutting head portion defining an end opening and a cutting edge at said end opening;
  - a body portion having a length from a proximal end adjacent said cutting head portion to an opposite distal end, said body portion defining a passageway along said length, said passageway sized to receive tissue excised by said cutting element, said distal end engageable to a drive source to reciprocate said tubular member within the outer tubular member; and
  - a hinge portion connecting said cutting head portion to said body portion to permit pivoting of said cutting head portion relative to said body portion when said cutting head portion contacts tissue extending through the cutting opening as said cutting member is advanced toward the tissue.

25. The cutting element according to claim 24, wherein said hinge portion defines an arc segment from a tubular form.

26. The cutting element according to claim 25, wherein said arc segment subtends an angle of between about 70 degrees and about 80 degrees (70–80°).

27. The cutting element according to claim 25, wherein said arc segment has a length dimension about one-fourth (¼) the diameter of said tubular cutting head portion.

28. The cutting element according to claim 24, in which the cutting opening of the outer tubular member has a width dimension along the length of said tubular member, wherein:
- said cutting head portion has a length dimension along the length of said body that is at least equal to the width dimension of the cutting opening.

29. The cutting element according to claim 24, wherein said hinge portion includes a diametrical slot extending through about 90% (ninety percent) of the diameter of said tubular member.

* * * * *